United States Patent [19]

Reifschneider

[11] Patent Number: 4,804,682

[45] Date of Patent: Feb. 14, 1989

[54] 2-CHLORO-4-((CYANOMETHYL)THIO)PHENYL N-METHYL CARBAMATE FOR TREATING CARCINOMAS

[75] Inventor: Walter Reifschneider, Walnut Creek, Calif.

[73] Assignee: Merrell Dow Pharmaceuticals Inc., Cincinnati, Ohio

[21] Appl. No.: 930,838

[22] Filed: Nov. 14, 1986

[51] Int. Cl.4 .................. A61K 31/275; C07C 121/52
[52] U.S. Cl. ...................................... 514/521; 558/396
[58] Field of Search ......................... 558/396; 514/521

[56] References Cited

PUBLICATIONS

Schicke et al., "Chem. Abst.", vol. 65, (1960), 7105a.

Primary Examiner—Anton H. Sutto
Attorney, Agent, or Firm—Louis J. Wille; Stephen L. Nesbitt

[57] ABSTRACT

The compound, 2-chloro-4-((cyanomethyl)thiolphenyl N-methyl carbamate, is a therapeutic agent in the treatment of patients afflicted with carcinomas or lymphocytic leukemia.

6 Claims, No Drawings

2-CHLORO-4-((CYANOMETHYL)THIO)PHENYL N-METHYL CARBAMATE FOR TREATING CARCINOMAS

BACKGROUND OF THE INVENTION

This invention relates to the novel compound 2-chloro-4-((cyanomethyl)thio)phenyl N-methyl carbamate which is useful as a therapeutic agent in the treatment of patients afflicted with a carcinoma or lymphocytic leukemia. In addition, this invention relates to a pharmaceutical composition containing the compound.

SUMMARY OF THE INVENTION

This invention relates to a novel compound, 2-chloro-4-((cyanomethyl)thio)phenyl N-methyl carbamate, and its use as a therapeutic agent in the treatment of certain specific neoplastic disease states in warm-blooded animals. A further aspect of this invention is a pharmaceutical composition so formulated as to make the compound bioavailable in warm-blooded animals in amounts effective in the treatment of the neoplastic disease states.

Neoplastic diseases in warm-blooded animals, which are characterized by rapidly proliferating cell growth, are recognized throughout the world as serious and lifethreatening disease states. These diseases have been and continue to be the subject of worldwide research efforts directed toward the identification of therapeutic agents effective in prolonging the survivability of the afflicted animal, in inhibiting cell growth of the neoplasm, and in effecting regression of the neoplasm. This research is primarily focused toward identifying agents which would be therapeutically effective in humans. Typically, compounds are screened for antineoplastic activity in small mammals, such as mice, in experiments designed to be predictive of antineoplastic activity not only in those animals but also in humans as against specifically identifiable human neoplastic disease states.

As used herein, the term "therapeutic agent" means a compound which when administered to a patient afflicted with a particular identified disease produces a beneficial effect in inhibiting or reversing the progression of the disease. A therapeutic agent for neoplastic diseases, such as carcinoma and lymphocytic leukemia, is a compound which when administered to the patient slows or stops the rapidly proliferating cell growth or causes regression of the cell growth or increases the survivability of the patient beyond that expected in the absence of the administration of the agent.

As used herein, the term "patient" means warm-blooded animals such as mammals, for example, dogs, rats, mice, cats, guinea pigs, horses, bovine cows, sheep and humans, which are afflicted with a neoplastic disease, for example, a carcinoma or lymphocytic leukemia.

As used herein, the term "neoplastic disease" means an abnormal state or condition in a warm-blooded animal characterized by rapidly proliferating cell growth or neoplasm.

As used herein, the term "carcinoma" means a malignant neoplasm made up of epithelial cells tending to infiltrate the surrounding tissues and give rise to metastases. Carcinomas tend to become progressively worse and result in death if left unchecked.

As used herein, the designation "(I)" means the compound 2-chloro-4-((cyanomethyl)thio)phenyl N-methyl carbamate.

Generally, 2-chloro-4-((cyanomethyl)thio)phenyl N-methyl carbamate can be utilized as a therapeutic agent in the treatment of patients afflicted with a carcinoma (treatment of breast or lung carcinoma is preferred) or a lymphocytic leukemia. As a therapeutic agent, (I) produces a beneficial effect in inhibiting or reversing the progression of the carcinoma or lymphocytic leukemia when administered in effective amounts to a patient afflicted with such a disease. This beneficial effect can be a slowing or stopping of the rapidly proliferating cell growth which characterizes these disease states, or a regression of such cell growth, or an increase in survivability of the patient beyond that expected in the absence of the administration of (I).

The therapeutic effect of (I) in the treatment of patients afflicted with a carcinoma or lymphocytic leukemia can be determined by performing tests utilized in the Developmental Therapeutics Program of the Division of Cancer Treatment of the National Cancer Institute (NCI) of the United States. In vivo evaluations in mice can be performed in order to determine antineoplastic activity in a variety of tumor systems including intraperitoneally-implanted P-388 leukemia (NCI Protocol 3PS31), subrenal capsule implanted human LX-1 lung carcinoma xenograft (NCI Protocol 3LKG5), and subrenal capsule implanted human MX-1 mammary carcinoma xenograft (NCI Protocol 3MBG5).

In these test systems the various cancers are developed in mice by the introduction of malignant tissues by implantation or grafting procedures. Implantation of these tissues can be by intraperitoneal (i.p.), subcutaneous (s.c.), or intravenous (i.v.) injection. Grafting can be by introduction of a tumor fragment under the kidney capsule. Animals are treated by injection of various dose regimens of test medication and antineoplastic activity is determined by mean survival time or by mean tumor weight change in comparison to a control group which receives no active treatment after transfer of the cancerous tissue. Specific criteria for the results of each test are established by the Developmental Therapeutics Program of the National Cancer Institute. These criteria delineate guidelines for the determination that a compound is "active" or "inactive" as a therapeutic agent in the particular disease state being studied. These guidelines generally require that the results in key variables of the animals receiving the test compound be a defined degree of improvement over that seen in those variables in the control group. These guidelines not only establish that a test compound is a therapeutic agent in the particular animal and neoplastic disease being studied, but also are meant to be predictive of clinical activity of the compound in humans or other mammals afflicted with similar neoplastic diseases.

As described in detail in the examples below, (I) was found to be an active therapeutic agent in the P-388 leukemia test (NCI Protocol 3PS31), the LX-1 lung carcinoma xenograft test (NCI Protocol 3LKG5) and the MX-1 mammary carcinoma xenograft test (NCI Protocol 3MGB5). These results indicate that (I) is effective in increasing the survivability of mice afflicted with lymphocytic leukemia and in inhibiting or reversing the rapidly proliferating cell growth associated with human carcinomas in general, and human breast and lung carcinomas in particular, in mice in which these carcinomas were implanted. Since these tests are indicative of similar activity in humans and other warm-blooded animals, these results predict similar therapeutic activity in humans or other warm-blooded animals afflicted with these particular neoplastic disease states.

An effective therapeutic dose of 2-chloro-4-((cyanomethyl)thio)phenyl N-methyl carbamate to be administered to patients afflicted with a carcinoma or lymphocytic leukemia is that amount and regimen which is effective in prolonging survivability of the patient, or in inhibiting the rapidly proliferating cell growth, or in facilitating regression of the size of the neoplasm.

A therapeutically effective dose cannot be absolutely determined, but is a function of a number of factors including, but not limited to, the species of mammal, its size, age and general health, the specific malignant neoplasm involved, the degree of involvement, the stage of development of the neoplasm, the mode of administration, the bioavailability characteristics of the preparation administered, the dose regimen selected, and use of concomitant medication. The correct amount for any specific situation can be readily determined by those skilled in the art using conventional range finding techniques and analogous results observed under other circumstances. A therapeutically-effective amount of (I) will vary from about 100 milligrams of (I) per kilogram of body weight per day (mg/kg/day) to about 2400 mg/kg/day and preferably will be about 1000 mg/kg/day to about 2400 mg/kg/day.

(I) can be administered to patients in any manner which makes (I) bioavailable in effective amounts, including orally or parenterally, for example, by intraperitoneal (i.p.), subcutaneous (s.c.), or intravenous injection (i.v.).

In general, the above compound is preferably administered in the form of a composition comprising the compound in admixture with one or more pharmaceutically acceptable carriers and excipients. Pharmaceutically acceptable carriers and excipients are substances that are chemically inert to the active compound and have no detrimental side effects or toxicity to mammals under the conditions of use. Suitable carriers and excipients include solvents such as water, alcohol, and propylene glycol, solid absorbants and diluents, surface active agents, suspending agents, tableting binders, lubricants, flavors, colorants, and the like. Such carriers and excipients are known to those in the art and are disclosed, for example, in texts such as Remington's Pharmaceutical Manufacturing, 13th Edition, Mack Publishing Co., Easton, Pa. (1965).

Compositions may be liquids such as suspensions or solutions or solids such as tablets, capsules, granulations, powders, and feed mixes, and may be designed for administration parenterally or orally.

The concentrations of the active ingredient, 2-chloro-4-((cyanomethyl)thio)phenyl N-methyl carbamate, in these pharmaceutical compositions are those which can be used in a therapeutically effective dose regimen and which are suitable for administration to mammals. Preferred compositions include those containing from about 0.0001 to about 50 percent by weight of the active compound. Those containing from about 0.001 to about 10 percent by weight are especially preferred.

Generally, 2-chloro-4-((cyanomethyl)thio)phenyl N-methyl carbamate can be prepared by reacting 2-chloro-4-(mercapto)phenol with chloroacetonitrile and a Lewis base. The Lewis base can be an alkali-metal methoxide and is preferably sodium methoxide. The resulting 2-chloro-4-((cyanomethyl)thio)phenol is isolated and reacted with methyl isocyanate in an inert solvent such as methylene chloride, chloroform, diethyl ether, tetrahydrofuran, benzene, or toluene among others with methylene chloride being preferred. It is preferred that the reaction be carried out in the presence of triethylamine (TEA) in catalytic amounts, i.e., an amount effective in accelerating the reaction time. The reaction is preferably carried out at ambient temperature, but the reaction also proceeds well at lower temperatures such as 5° C. and at higher temperatures such as the reflux temperature of the solvent.

The preparation and use of the present invention is exemplified as follows:

EXAMPLE 1

Preparation of 2-chloro 4-((cyanomethyl)thio)phenyl N-methyl carbamate

To a stirred sodium methoxide solution prepared from 4.6 grams (g) of sodium and 200 milliliters (ml) of methanol, was added 31.2 g of 2-chloro-4-(mercapto)phenol and to the resulting mixture, 16 g of chloroacetonitrile was added dropwise. The mixture was stirred overnight at ambient temperature. The resulting 2-chloro-4-((cyanomethyl)thio)phenol was extracted into ether, washed, and dried over anhydrous $Na_2SO_4$. After stripping off the solvent the above phenol was recrystallized from toluene and gave a melting point of 106.5°–108.5 degrees Centegrade (°C). To 28.5 g of the above phenol in 200 ml of methylene chloride was added 9 g of methyl isocyanate and 3 drops of TEA. The reaction was allowed to proceed at ambient temperature and crystals of 2-chloro-4((cyanomethyl)thio)phenyl N-methyl carbamate were collected and recrystallized from methylene chloridehexane to yield 33.4 g of (I) with a melting point of 114°–116° C.

EXAMPLE 2

Intraperitoneally-implanted P388 Leukemia Test (NCI Protocol 3PS31)

Male $CD_2F_1$ mice, within a 3 gram body weight range with a minimum weight of 18 grams, were implanted intraperitoneally with about $1 \times 10^6$ P388 leukemia cells harvested from DBA/2 mice in which this leukemia cell line is propagated. This leukemia cell line was chemically induced originally in 1955 in a DBA/2 mouse by painting the skin with 3-methylcholanthrene. Beginning one day after tumor implant, the animals were injected i.p. once every four days, for a total of three injections, with (I) at one of various doses or with a control solution containing no test agent. The control group and the test agent groups at each individual dose level were made up of six animals each. The median survival time for each group was calculated. In two separate experiments, the median survival time for the group which received 200 mg/kg/injection of (I) was 131% and 135% of the median survival time of the control group. By NCI standards, a median survival time $\geq 120\%$ of that of the control group is considered to be indicative of an active compound.

EXAMPLE 3

Subrenal Capsule Implanted Human Lung LX-1 Xenograft Test (NCI Protocol 3LKG5)

Athymic Swiss (Cr:NIH(S)-nu) or athymic random bred (NCr-nu) mice, within a four gram body weight range with a minimum weight of 18 grams for males and 17 grams for females, were implanted under the membranous covering of the kidney with a tumor fragment of recorded dimensions approximately 1 millimeter (mm)×1 mm×1 mm. This tumor fragment was propagated in mice from a subcutaneous metastatic tumor from a human with oat cell lung carcinoma. Beginning one day after tumor implant, the animals were injected s.c. once every four days, for a total of three injections with (I) at one of various doses or with a control solution containing no test agent. The control group consisted of 14 animals and the test agent groups at each individual dose level consisted of six animals each. Two days after the last injection the animals were sacrificed and the tumor dimensions were recorded. The mean tumor weight change (Mean Tumor Weight Final - Mean Tumor Weight Initial) for each group was calculated based on the length and width measurements of the tumor. In two separate experiments, one involving male mice and one involving female mice, the mean tumor weight change for the groups which received 2400 mg/kg/injection were 15% (male) and 13% (female) of the mean tumor weight change in the corresponding control groups. By NCI standards, a mean tumor weight change of ≦20% of that recorded for control animals, is considered to be indicative of an active compound.

EXAMPLE 4

Subrenal Capsule Implanted Human Mammary Carcinoma MX-1 Xenograft (NCI Protocol 3MBG5)

Athymic Swiss (Cr:NIH(S)-nu) or athymic random bred (NCr-nu) mice, within a four gram body weight range with a minimum weight of 18 grams for males and 17 grams for females, were implanted under the membranous covering of the kidney with a tumor fragment of recorded dimensions, approximately 1 mm×1 mm×1 mm. This tumor fragment was propagated in mice from a human primary mammary tumor. Beginning one day after tumor implant, the animals were injected s.c. with (I) at one of various doses or with control solution containing no test agent. In one series of experiments, the animals were injected every day for a total of ten days. In another series of experiments animals were injected once every four days for a total of three injections. In each experiment, the control group consisted of 12 to 14 animals with the test agent group at each individual dose level consisting of four to 6 animals each. One or two days after the last dose, the animals were sacrificed and the tumor dimensions were recorded.

The mean tumor weight change (Mean Tumor Weight Final - Mean Tumor Weight Initial) for each group was calculated based on the length and width measurements of the tumor. When there is a net increase in tumor weight over the course of study, the NCI specifies the appropriate criteria for activity as the mean tumor weight change of the test group as a percentage of the mean tumor weight change of the control group. When there is a net decrease in tumor weight over the course of the study, the appropriate criteria is the mean tumor weight change as a percentage of initial mean tumor weight.

When (I) was dosed daily for a total of ten days, the test groups obtained a 30% to 58% decrease in mean tumor weight at 600 mg/kg/injection and a 33% to 59% decrease in mean tumor weight at 300 mg/kg/injection. The mean tumor weight change for the group which received (I) at 150 mg/kg/injection was 2% of the mean tumor weight change in the corresponding control group. When (I) was dosed every fourth day for a total of three injections, the test groups obtained a 0% to 60% decrease in mean tumor weight at 2400 mg/kg/injection, a 62% decrease in mean tumor weight at 1200 mg/kg/injection, and an 8% decrease in mean tumor weight at 600 mg/kg/injection. In another experiment, the mean tumor weight change for groups which received 300, 600 and 1200 mg/kg/injection was 3 to 4% of mean tumor weight change in the corresponding control group. By NCI standards, a mean tumor weight change which is ≦20% of the mean tumor weight change of the control group is considered to be indicative of an "active" compound.

I claim:

1. 2-Chloro-4-((cyanomethyl)thio)phenyl N-methyl carbamate.

2. A method for treating patients afflicted with carcinomas which comprises administering thereto an effective therapeutic amount of 2-chloro-4-((cyanomethyl)thio)phenyl N-methyl carbamate.

3. A method according to claim 2 wherein the carcinoma comprises a breast carcinoma.

4. A method according to claim 2 wherein the carcinoma comprises a lung carcinoma.

5. A method for treating patients afflicted with lymphocytic leukemia which comprises administering thereto an effective therapeutic amount of 2-chloro-4-((cyanomethyl)thio)phenyl N-methyl carbamate.

6. A pharmaceutical composition which comprises an effective therapeutic amount of 2-chloro-4-((cyanomethyl)thio)phenyl N-methyl carbamate and one or more pharmaceutically acceptable carriers or excipients.

* * * * *